United States Patent [19]

Askin et al.

[11] Patent Number: 5,496,948
[45] Date of Patent: Mar. 5, 1996

[54] PROCESS FOR MAKING HIV PROTEASE INHIBITORS

[75] Inventors: David Askin, Warren; Kan K. Eng, Jersey City; Ralph P. Volante, Cranbury, all of N.J.

[73] Assignee: Merck & Co., Inc., Rahway, N.J.

[21] Appl. No.: 459,069

[22] Filed: Jun. 21, 1995

Related U.S. Application Data

[60] Division of Ser. No. 187,664, Jan. 26, 1994, which is a continuation-in-part of Ser. No. 93,225, Jul. 16, 1993, abandoned.

[51] Int. Cl.⁶ .................................................. C07D 241/02
[52] U.S. Cl. ...................... 544/368; 544/349; 544/360; 544/365; 544/117; 544/119; 544/120; 544/121; 544/124; 544/128; 544/131; 544/137; 546/146; 546/270; 548/217
[58] Field of Search ................... 544/368, 349, 544/360, 365, 117, 119, 120, 121, 124, 128, 131, 137; 546/146, 270; 548/217

[56] References Cited

PUBLICATIONS

CA 116:256007a Highly . . . HIV-1 protease, Askin et al., pp. 835-836, 1992.
CA 119:9166s Stereo selective . . . epoxides. Askin et al., p. 947, 1993.

*Primary Examiner*—Joseph K. McKane
*Attorney, Agent, or Firm*—Roy D. Meredith; Carol S. Quagliato; Melvin Winokur

[57] ABSTRACT

Intermediates of structural formula

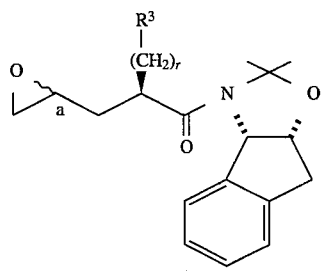

can be made by reacting glycidol or an activated derivative thereof with an amide. The process and intermediates are useful for synthesizing HIV protease inhibitor compounds.

7 Claims, No Drawings

PROCESS FOR MAKING HIV PROTEASE INHIBITORS

This is a division of application Ser. No. 08/187,664 filed Jan. 26, 1994, now allowed which is a continuation-in-part of 08/093,225, filed Jul. 16, 1993, now abandoned

BACKGROUND OF THE INVENTION

The present invention is concerned with a novel intermediate and process for synthesizing compounds which inhibit the protease encoded by human immunodeficiency virus (HIV), and in particular L-735,524, or pharmaceutically acceptable salts thereof. These compounds are of value in the prevention of infection by HIV, the treatment of infection by HW and the treatment of the resulting acquired immune deficiency syndrome (AIDS).

More specifically, the instant process involves the reaction of an amide enolate derived from an amide, such as N-(2(R)-hydroxy-1(S)-Indanyl)-3-phenylpropaneamide, with an activated nonracemic glycidol derivative, such as 2(S)-glycidyl tosylate, to afford an epoxide intermediate which is a key intermediate useful in the preparation of HIV protease inhibitor compounds, including L-735,524. Also provided is an improved process for the synthesis of specific dialkylamines used in the synthesis of HIV protease inhibitors.

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313,277 (1985)]. Amino acid sequence homology provides evidence that the pol sequence encodes reverse transcriptase, an endonuclease and an HIV protease IToh, H. et al., *EMBO J.*, 4, 1267 (1985); Power, M.D. et al., *Science*, 231, 1567 (1986); Pearl, L. H. et al., *Nature*, 329, 351 (1987)]. The end product compounds, including L-735,524 which is shown in Example 4 below,that can be made from the novel intermediates and process of this invention are inhibitors of HIV protease, and are disclosed in EPO 541, 168, which published on May 12, 1993.

Previously, the synthesis of L-735,524 and related compounds was accomplished via a 12-step procedure which employed a hydroxy protected dihydro-5(S)-hydroxymethyl-3(2H) furanone which was alkylated, and involved replacement of an alcohol leaving group on the alkylated furanone with a piperidine moiety. The coupled product was then hydrolyzed to open the furanone ring into a hydroxy acid moiety, and the acid was ultimately coupled to 2(R)-hydroxy-1(S)aminoindane. This procedure is described in EPO 541,168. The extreme length of this route (12 steps), renders this process time consuming and labor intensive, and it requires the use of many expensive reagents and an expensive starting material. A route requiring fewer reaction steps and reagents would provide desirable economical and time-saving benefits.

A modified route to L-735,524 and related compounds was also shown in EPO 541,168 based on the diastereoselective alkylation of the enolate derived from N-(2(R)-hydroxy-1(S)-indan-N,O-isopropylidene-yl)-3-phenyl-propaneamide, in which the C3-C5 three-carbon unit was introduced as an allyl group and later oxidized. Some problems with this route are: (a) four steps are necessary to effect the introduction of the three carbon glycidyl fragment, (b) highly toxic $OsO_4$ is used in the process and (c) low diastereoselectivity is obtained in the dihydroxylation step. Thus, a desirable process would directly introduce the three carbon unit in the correct chiral oxidized form.

Furthermore, the synthesis of the chiral piperazine intermediate was effected from 2-pyrazinecarboxylic acid in a 6 step procedure and required the use of expensive reagents such as BOC-ON and EDC. A shorter route to the piperazine intermediate which also does not use expensive reagents would thus be desired.

Several examples of condensations of stabilized carbanions with glycidol and its derivatives (activated or unactivated) are known in the literature; however, no known methods produce a new epoxide directly in good yield. See, e.g., Hanson, R. M., *Chem. Rev.*, 1991, 91,437–475. In the case of activated glycidol derivatives and carbon nucleophiles, this is due primarily to the anticipated and undesirable "double" addition of the nucleophile to the epoxide product. Furthermore, none of the known examples have an amide moiety as the carbanion stabilizing group (amide enolate) and additionally, no known examples involve the coupling of a stabilized carbanion bearing chirality to chiral, non-racemic glycidol derivatives (double diastereoselection).

Condensations of stabilized carbanions with activated nonracemic glycidol derivatives have been demonstrated: malonate anion has been coupled with both non-racemic epichlorohydrin i and nonracemic glycidyl triflate ii to afford the cyclopropyl-lactone iii. See, e.g., Pimmg, M. C., et al., *Helvetica Chimica Acta* 1989, 72, 1301–1310, and Burgess, K., et al., *J. Org. Chem.* 1992, 57, 5931–5936. Thus, in this case, the intermediate epoxide undergoes further reaction to afford the cyclopropyl ring system. In the case of i, the initial reaction with malonate anion occurs at the epoxide terminus ($C_3$), whereas with ii, the initial reaction occurs at the triflate $C_1$ terminus.

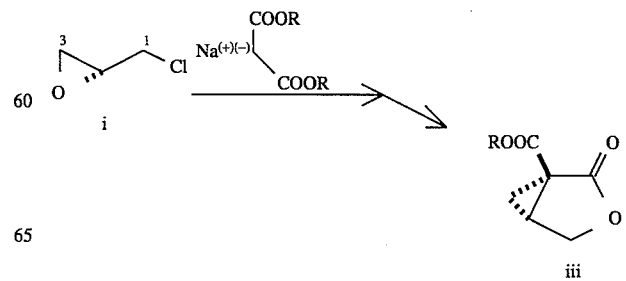

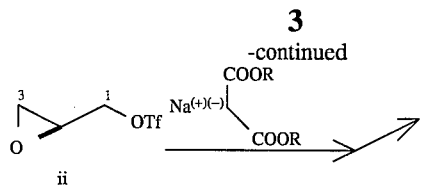

ii

A related example is reaction of sulfone-stabilized carbanion derived from v with glycidyl tosylate iv to afford the hydroxy-tosylate vi. See, e.g., Baldwin, J. E., et al., *J. Chem. Soc., Chem. Commun.* 1992, 1249–1251. In this case, although double addition of the carbanion is not a major problem, an additional step is necessary to convert the intermediate hydroxy-tosylate vi to the desired epoxide.

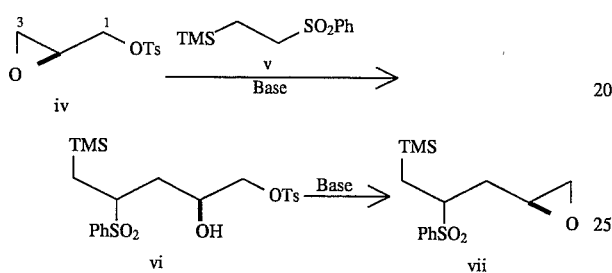

Similarly, it is unknown in the literature and unexpected that nitrogen nucleophiles can be selectively added to activated glycidol derivatives in good yield without the problematic double addition.

Also known in the art is the condensation of amide enolates derived from N-(2(R)-hydroxy-1(S)-indan-N,O-isopropylidene-yl)-3-phenylpropaneamide 1 with protected alpha-amino epoxides viii to afford the desired hydroxyethylene dipeptide isostere intermediates ix with a high degree of stereocontrol for the $C_2$-(R)-stereocenter. See, e.g., Askin, D., et al., *J. Org. Chem.*, 1992, 57, 2771–2773 and U.S. Pat. No. 5,169,952 to Askin, D., et al.. After hydrolysis, the deprotected hydroxyethylene dipeptide isostere inhibitors are obtained.

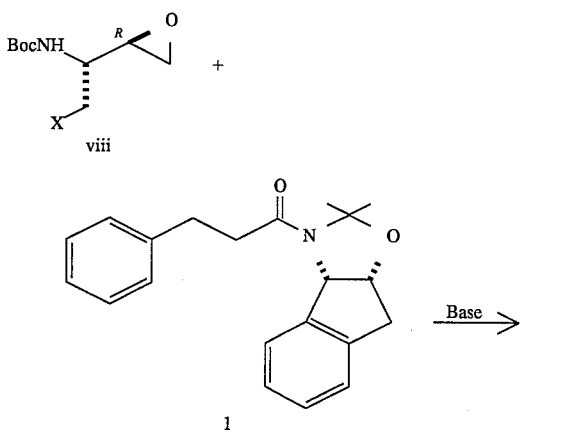

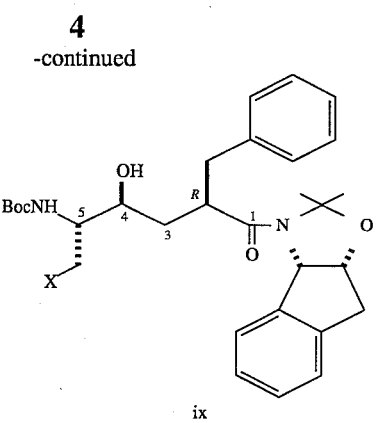

ix

The resolution of 2-piperazinecarboxylic acid with (+)-CSA is known. See. e.g., Felder, E., et al., *Helvetica Chim. Acta,* 1960, 43, 888. However, examples of the resolution of piperazine amides are not known in the literature.

The instant invention provides a more advantageous method for preparing HIV protease inhibitors than previously known. It allows a much shorter, more highly diastereoselective, higher yielding synthesis of the compounds disclosed in EPO 541,168, and in particular L-735,524, without the use of toxic reagents such as osmium tetraoxide or prohibitively expensive reagents such as (S)-(+)-dihydro-5-(hydroxymethyl)-2(3H)-furanone.

SUMMARY OF THE INVENTION

The instant invention involves novel synthetic methods for making epoxide intermediates such as 3, which are useful for the synthesis of HIV protease inhibitors. The invention involves the reaction of an amide enolate, such as the enolate derived from 1, with an activated nonracemic glycidol derivative, such as 2(S)-glycidyl tosylate 2, to afford an epoxide product such as 3 in one step and in good yield. The result of this reaction is unexpected since epoxide 3 was predicted to undergo further reaction under the coupling conditions to afford a large amount of the dimer product 3-a, thus giving poor yields of 3.

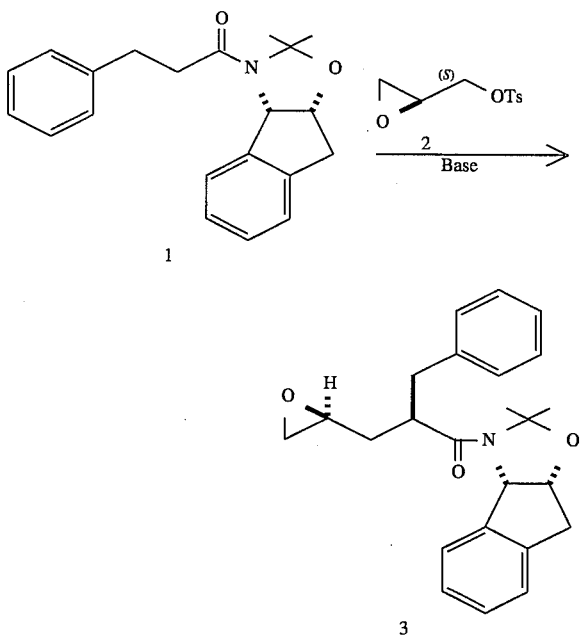

-continued

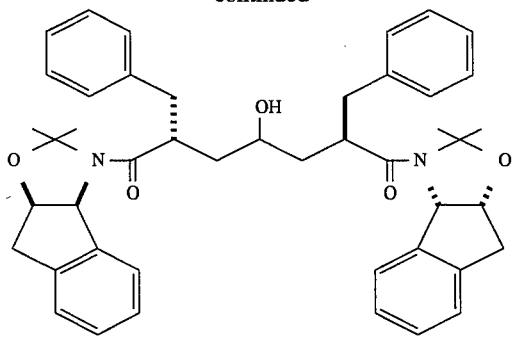

3-a

The invention further involves epoxide intermediate compounds and the coupling of the epoxide intermediate with an amine of formula V, defined below, to form HIV protease intermediates and final products.

Some abbreviations that may appear in this application are as follows.

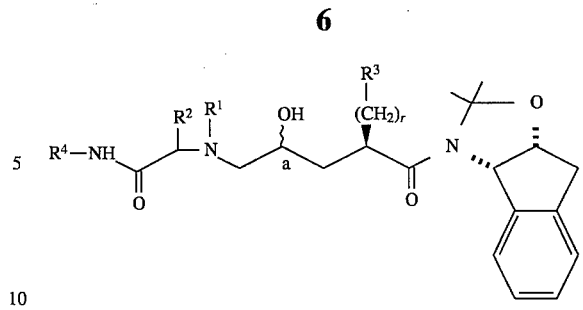   I comprises the steps of:

(1) reacting either a. a glycidol of formula II

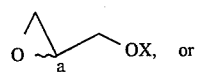   II b. epichlorohydrin, of the structure

| Designation | ABBREVIATIONS |
|---|---|
| | Protecting Group |
| BOC (Boc) | t-butyloxycarbonyl |
| CBZ (Cbz) | benzyloxycarbonyl (carbobenzoxy) |
| TBS (TBDMS) | t-butyl-dimethylsilyl |
| | Activating Group |
| Ts or tosyl or tosylate | p-toluenesulfonyl |
| Ns or nosyl or nosylate | 3-nitrobenzenesulfonyl |
| Tf or triflyl or triflate | trifluoromethanesulfonyl |
| Ms or mesyl or mesylate | methanesulfonyl |
| | Coupling Reagent |
| BOP reagent | benzotriazol-1-yloxytris(dimethylamino)-phosphonium hexafluorophosphate |
| BOP-Cl | bis(2-oxo-3-oxazolidinyl)phosphinic chloride |
| EDC | 1-ethyl-3-(3-dimethylaminopropyl) carbodiimide hydrochloride |
| | Other |
| BOC-ON | 2-(tert-butylcarbonyloxyimino)-2-phenylacetonitrile |
| (BOC)₂O (BOC₂O or Boc₂O) | di-t-butyl dicarbonate |
| n-Bu₄N⁺F⁻ | tetrabutyl ammonium fluoride |
| nBuLi (n-Buli) | n-butyllithium |
| (S)-CSA | (1S)-(+)-10-camphorsulfonic acid |
| DIEA or DIPEA | diisopropylethylamine |
| DMAP | dimethylaminopyridine |
| DME | dimethoxyethane |
| DMF | dimethylformamide |
| Et₃N | triethylamine |
| EtOAc | ethyl acetate |
| h | hour(s) |
| IPA | 2-propanol |
| LDA | lithium diisopropylamide |
| L-PGA | (L)-pyroglutamic acid |
| TFA | trifluoroacetic acid |
| THF | tetrahydrofuran |
| TLC | thin layer chromatography |

DETAILED DESCRIPTION OF THE INVENTION

The instant invention provides a novel process for making intermediates of formulas I and IV which are useful in the preparation of HIV protease inhibitors, and in particular those compounds disclosed in EP0 541,168. The process for making intermediates of formula I

with an amide of formula III

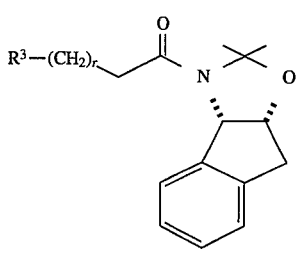

in the presence of a strong base at low temperature to produce the adduct IV

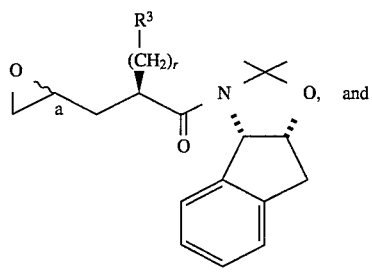

(2) reacting IV with an amine of formula V to produce I

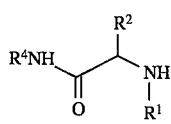

wherein:
stereocenter a is in either the R configuration, the S configuration or is racemic;
X is selected from the group consisting of -H, methanesulfonyl, trifluoromethanesulfonyl, p-toluenesuffonyl, benzenesulfonyl, and 3-nitrobenzenesulfonyl;
r is an integer from zero through and including 5;
$R^1$ and $R^2$ are independently selected at each occurrence from the group consisting of:
1) hydrogen,
2) —$C_{1-4}$ alkyl unsubstituted or substituted with one or more of
 a) hydroxy,
 b) $C_{1-3}$ alkoxy,
 c) aryl unsubstituted or substituted with one or more of $C_{1-4}$ alkyl, hydroxy or aryl,
 d) —W-aryl or —W-benzyl, wherein W is —O—, or —S—,
 e) a 5–7 membered cycloalkyl group unsubstituted or substituted with one or more of
  i) hydroxy,
  ii) $C_{1-3}$ alkoxy, or
  iii) aryl,
 f) heterocycle unsubstituted or substituted with one or more of hydroxy, $C_{1-4}$alkyl, $C_{1-4}$alkyl substituted with hydroxy, or Boc,
 g) —NH—COO$C_{1-3}$alkyl
 h) —NH—CO—$C_{1-3}$alkyl,
 i) —NH—$SO_2C_{1-3}$alkyl,
 j) —COOR, or
 k) —(($CH_2)_mO)_nR$, or
3) aryl unsubstituted or substituted with one or more of
 a) halo,
 b) hydroxy,
 c) —$NO_2$ or —$N(R)_2$,
 d) $C_{1-4}$alkyl,
 e) $C_{1-3}$ alkoxy, unsubstituted or substituted with one or more of —OH or $C_{1-3}$ alkoxy,
 f) —COOR,
 g) —$CON(R)_2$,
 h) —$CH_2N(R)_2$,
 i) —$CH_2NHCOR$,
 j) —CN,
 k) —$CF_3$,
 l) —NHCOR,
 m) aryl $C_{1-3}$ alkoxy,
 n) aryl,
 o) —$NRSO_2R$,
 p) —$OP(O)(OR_x)_2$, or
 q) —$R^5$, as defined below; or $R^1$ and $R^2$ can be joined together with the nitrogen to which $R^1$ is attached and the carbon to which $R^2$ is attached to form a 3 to 10 membered monocyclic or bicyclic saturated ring system which consists of the nitrogen to which $R^1$ is attached and from 2 to 9 carbon atoms suchn as for example

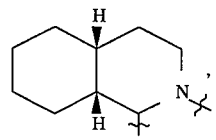

and is unsubstituted or substituted with one or more of:
1) hydroxy,
2) $C_{1-4}$ alkyl unsubstituted or substituted with one or more of
 a) halo,
 b) hydroxy,
 c) $C_{1-3}$ alkoxy,
 d) aryl,
 e) a 5–7 membered cycloalkyl group unsubstituted or substituted with one or more of
  i) hydroxy,
  ii) $C_{1-3}$ alkoxy, or
  iii) aryl, or
 f) heterocycle,
3) $C_{1-3}$alkoxy,
4) —NH—COO$C_{1-3}$alkyl,
5) —NH—CO—$C_{1-3}$ alkyl,
6) —NH—$SO_2C_{1-3}$alkyl,
7) heterocycle,
8) —W—aryl, or
9) —W—CO-aryl,
wherein W is defined above; or $R^1$ and $R^2$ can be joined together with the nitrogen to which $R^1$ is attached and the carbon to which $R^2$ is attached to form a 3 to 10 membered monocyclic or bicyclic saturated ring system which consists of the nitrogen to which $R^1$ is attached, from 1 to 8 carbon atoms and one or more unsubstituted or substituted heteroatom selected from 1) 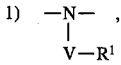

wherein V is absent or —CO—Q— or —$SO_2$—Q—,
$R^1$ is defined as above for when $R^1$ is independent from and not joined to $R^2$,
and wherein Q is absent or —O—, —N(R)—, or heterocycle optionally substituted with —$C_{1-4}$alkyl, 2) 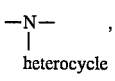

3) —N—
   |
   C$_{1-4}$alkenyl, unsubstituted or substituted with aryl

4) —N—
   |
   SO$_2$—C$_{1-4}$alkenyl, unsubstituted or substituted with aryl

5) —S(O)$_p$—, where in p is zero, 1 or 2, or

6) —O—, such as, for example,

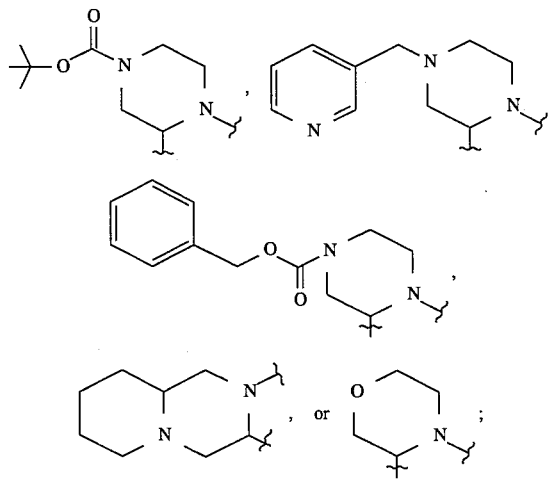

R$^3$ is selected from the group consisting of:
1) hydrogen,
2) —C$_{1-4}$ alkyl
3) C$_5$–C$_{10}$ cycloalkyl, optionally substituted with hydroxy,
4) C$_6$–C$_{10}$ aryl, unsubstituted or substituted with one or more of:
   a) halo,
   b) hydroxy,
   c) —NO$_2$ or —N(R)$_2$,
   d) C$_{1-4}$ alkyl,
   e) C$_{1-3}$ alkoxy, unsubstituted or substituted with one or more of —OH or C$_{1-3}$ alkoxy,
   f) —COOR,
   g) —CON(R)$_2$,
   h) —CH$_2$N(R)$_2$,
   i) —CH$_2$NHCOR,
   j) —CN,
   k) —CF$_3$,
   l) —NHCOR,
   m) aryl C$_{1-3}$ alkoxy,
   n) aryl,
   o) —NRSO$_2$R,
   p) —OP(O)(OR$_x$)$_2$, or
   q) —R$^5$, as defined below, or
5) monocyclic or bicyclic heterocycle containing from 1 to 3 heteroatoms chosen from the group consisting of N, O, and S, such as, for example, 2-pyridyl, 3-pyridyl, or 4-pyridyl, and which is unsubstituted or substituted with R$^5$ and optionally with one or more of
   a) halo,
   b) C$_{1-4}$ alkyl, or
   c) C$_{1-3}$ alkoxy;

m is 2, 3, 4 or 5;

n is zero, 1, 2 or 3;

R is hydrogen or C$_{1-4}$ alkyl;

R$_x$ is H or aryl;

R$^4$ is C$_{1-5}$ alkyl, straight or branched chain; and

R$^5$ is
1) —W—(CH$_2$)$_m$—NR$^6$R$^7$ wherein W and m are defined above, and R$^6$ and R$^7$ are independently selected at each occurrence from:
   a) hydrogen,
   b) C$_{1-6}$ alkyl, unsubstituted or substituted with one or more of
      i) C$_{1-3}$ alkoxy,
      ii) —OH, or
      iii) —N(R)$_2$,
   c) aromatic heterocycle unsubstituted or substituted with one or more of
      i) C$_{1-4}$ alkyl, or
      ii) —N(R)$_2$,
   d) or R$^6$ and R$^7$ are joined together with the nitrogen to which they are attached to form a 5–7 member heterocycle, such as morpholino, containing up to two additional heteroatoms selected from —N(R), —O—, —S—, —S(O)— or —S(O)$_2$—, the heterocycle optionally substituted with C$_{1-4}$ alkyl,
2) —(CH$_2$)$_q$—NR$^6$R$^7$ wherein q is an integer from 1–5, and R$^6$ and R$^7$ are defined above, except that R$^6$ or R$^7$ are not H or unsubstituted C$_{1-6}$ alkyl, or
3) benzofuryl, indolyl, azacycloalkyl, azabicyclo C$_{7-11}$ cycloalkyl, or benzopiperidinyl, unsubstituted or substituted with C$_{1-4}$ alkyl.

Scheme 1 below, illustrates this process. However, the instant process is not limited by any particular substituents employed in the scheme which are used for the purpose of illustration.

SCHEME 1

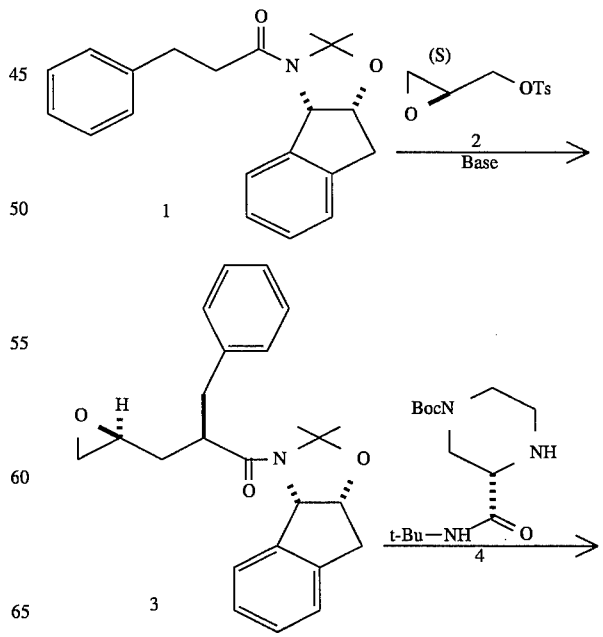

-continued
SCHEME 1

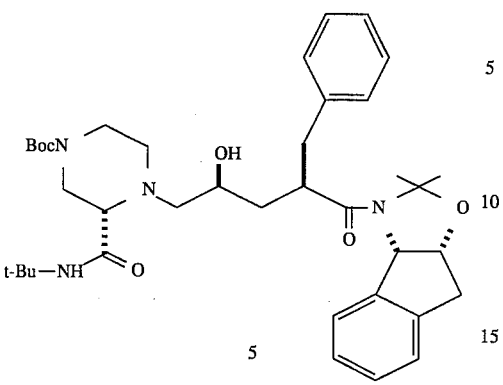

5

Intermediates of formula IV are synthesized by reacting glycidol or its derivative II and amide III in the presence of a strong base. The strong base must be a metal-containing base, and may or may not be in an inert anhydrous organic solvent, such as, e.g., cyclic or acyclic hydrocarbons including hexane, pentane, cyclohexane, etc. Suitable strong bases include: $LiN[(CH_3)_3Si]_2$, $KN[(CH_3)_3Si]_2$, $NaN[(CH_3)_3Si]_2$, n-butyllithium (n-BuLi), s-BuLi, t-BuLi, potassium tert-butoxide, lithium diisopropylamide (LDA), lithium isopropylcyclohexylamide, lithium pyrrolidide, lithium tetramethylpiperidide, phenyllithium, isopropylmagnesium chloride, isobutylmagensium chloride, and other similar strong base known in the art. Preferred strong bases are n-BuLi, s-BuLi, $LiN[(CH_3)_3Si]_2$ and LDA, with n-BuLi and $LiN[(CH_3)_3Si]_2$ being most preferred. Preferably, about 1 to 2 molar equivalents of strong base are used per 1 molar equivalent of III, with a ratio of about 1.15:1 molar equivalents of base:III being most preferred. The reaction of II with III can be done by combining II and III in one pot and then adding the strong base, or it can be done sequentially, i.e., by first treating amine III with base followed by addition of II. The strong base effects metalation of the amide III at the position alpha to the carbonyl group to afford the reactive metal amide enolate which then effects ring opening of the epoxide II at the terminal position to afford the product IV. A new center of asymmetry is created in the product isostere IV at the 2-position.

The reaction is preferably run at a low temperature, for example ranging between about −82° C. and 0° C. To effect metalation of the amide III, the temperature range is maintained more preferably between about −82° C. and −40° C., and most preferably between about −50° C. and −45° C. To effect the reaction of the metalated amide and II to form IV, the temperature range is maintained more preferably between about −50° C. and −10° C., and most preferably between about −30° to −20° C. for 4–5 hours.

Preferably, the reaction of II with III is run in an etherial solvent. The etherial solvents are any solvents suitable for use in this reaction step including, e.g., tetrahydrofuran, 1,2-dimethoxyethane, diethyl ether and methyl-t-butyl ether or combinations thereof, with tetrahydrofuran being preferred.

Compounds of formula I are made by reacting a compound of formula IV with an amine of formula V. Preferably from about 1 to 3 molar equivalents of amine V are used per molar equivalent of epoxide IV, with a ratio of about 1.05:1 molar equivalents of V:IV being more preferred.

This reaction can be run in any suitable solvent, such as, e.g., one chosen from hydrocarbons, such as toluene, ethers such as diethyl ether, alcohols such as methanol, ethanol or isopropanol, nitriles such as acetonitrile, and esters such as ethyl acetate or combinations thereof, with alcohols being preferred and isopropanol being most preferred. The temperature of the reaction can be maintained in a range from ambient to the reflux temperature of the solvent used, but is preferably run at an elevated temperature, e.g., in the range of 80° C. to 90° C., and most preferably from about 83° C. to 85° C.

Activated glycidols of formula II can be prepared by methods known in the art, such as described in, e.g., J. Klunder, et al., *J. Org. Chem.*, 1989, 54, 1295–1304 and references cited therein.

Amide compounds of formula III can be made according to standard procedures known to those skilled in the art, such as, e.g., the procedure described in Example 1, using the appropriate starting materials.

Protecting groups such as nitrogen protecting groups may be used where appropriate in the practice of this invention. For example, the 4 position nitrogen of 2-t-butylcarboxamide piperazine may be protected with a group such as BOC, CBZ, benzyl, 4-methoxybenzyl, 2,4-dimethoxybenzyl, trifluoroacetamide, trialkylsilyl, or other groups known in the art.

End-product HIV protease inhibitors are made from compounds of formula I by removing any remaining protecting groups present according to deprotection methods well known to those skilled in the art. For example, the ketal protecting group can be removed by treating I with acid in the presence of methanol, or by aqueous acid or by 1N HCl in THF, to produce the final HIV protease inhibitor products. Compounds of formula I may also be further substituted by methods known in the art.

In one embodiment of this invention, stereocenter a has the S configuration; X is p-toluenesulfonyl; r is 1; $R^1$ and $R^2$ are joined together to form a cyclic structure selected from the group consisting of:

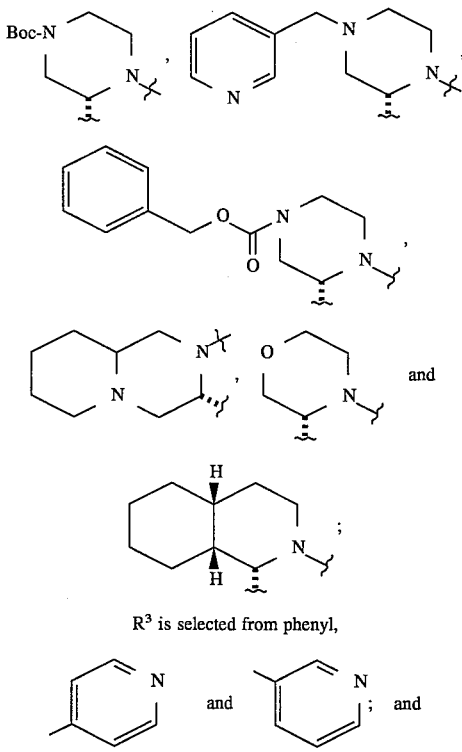

$R^4$ is tert-butyl.

Within this embodiment is the preferred species of formula II which is the intermediate compound of formula IV-a

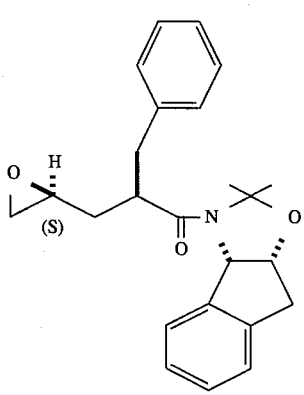

Also within this embodiment are the preferred species of formula I, which are the intermediate compounds of formulas I-a and I-b

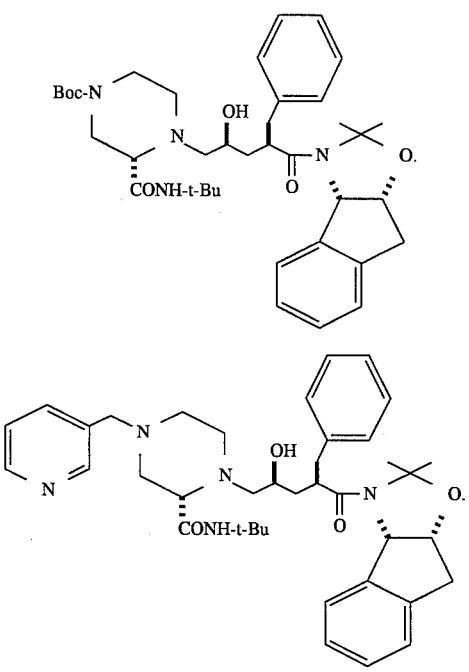

Compound I-b can be made by directly coupling the 2(S)-t-butylcarboxamide- 4N-(methyl-3-pyridyl)-piperazine with IV-a. Preferably, the final product L-735,524 is made by deprotection and picolylation of I-a, as exemplified in Examples 3–4.

The processes and intermediates of this invention are useful for the preparation of end-product compounds that are useful in the inhibition of HIV protease the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the end-product compounds that can be made from the processes and intermediates of this invention are useful in treating infection by HIV after suspected past exposure to HIV by, e.g., blood transfusion, organ transplant, exchange of body fluids, bites, accidental needle stick, or exposure to patient blood during surgery.

The end-product HIV protease inhibitors are also useful in the preparation and execution of screening assays for antiviral compounds. For example, end-product compounds are useful for isolating enzyme mutants, which are excellent screening tools for more powerful antiviral compounds. Furthermore, such compounds are useful in establishing or determining the binding site of other antivirals to HIV protease, e.g., by competitive inhibition. Thus the end-product compounds that are made from the processes and intermediates of this invention are commercial products to be sold for these purposes.

HIV protease inhibitor compounds that can be made from the intermediates and processes of the instant invention are disclosed in EPO 541,164. The HIV protease inhibitory compounds may be administered to patients in need of such treatment in pharmaceutical compositions comprising a pharmaceutical carrier and therapeutically-effective amounts of the compound or a pharmaceutically acceptable salt thereof. EPO 541,164 discloses suitable pharmaceutical formulations, administration routes, salt forms and dosages for the compounds.

The compounds of the present invention, may have asymmetric centers and occur as racemates, racemic mixtures and as individual diastereomers, or enantiomers with all isomeric forms being included in the present invention.

When any variable (e.g., aryl, heterocycle, R, $R^1$, $R^2$, n, X, etc.) occurs more than one time in any constituent or in formulas I-V, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl; t-Bu is tert-butyl); "alkoxy" represents an alkyl group of indicated number of carbon atoms attached through an oxygen bridge; and "cycloalkyl" is intended to include saturated ting groups, such as cyclopropyl, cyclobutyl, cyclopentyl, cyclohexyl (Cyh) and cycloheptyl. "Alkenyl" is intended to include hydrocarbon groups of either a straight or branched configuration with one or more carbon-carbon double bonds which may occur in any stable point along the chain, such as ethenyl, propenyl, butenyl, pentenyl, and the like. "Alkynyl" is intended to include hydrocarbon groups of either a straight or branched configuration with one or more carbon-carbon triple bonds which may occur in any stable point along the chain, such as ethynyl, propynyl, butynyl, pentynyl, and the like. "Halo", as used herein, means fluoro, chloro, bromo and iodo. As used herein, "aryl" is intended to mean phenyl (Ph) or naphthyl.

The term heterocycle or heterocyclic, as used herein except where noted, represents a stable 5- to 7-membered mono- or bicyclic or stable 7- to 10-membered bicyclic heterocyclic ting system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure. Examples of such heterocyclic elements include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

Representative experimental procedures utilizing the novel process are detailed below. These procedures are exemplary only and should not be construed as being limitations on the novel process of this invention.

EXAMPLE 1

Preparation of Amide 1

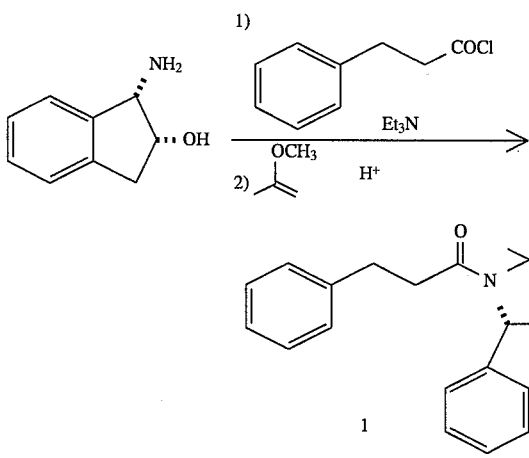

A solution of (−)-cis-1-aminoindan-2-ol (884 g, 5.93 mol) in 17.8 L of dry THF (KF=55 mg/mL) (KF stands for Karl Fisher titration for water) and triethylamine (868 mL, 6.22 mol) in a 50 L round bottom flask equipped with a thermocouple probe, mechanical stirrer, and a nitrogen inlet adapter and bubbler, was cooled to 15° C. Then, 3-phenylpropionyl chloride (1000 g, 5.93 mol) was added over 75 minutes, while the internal temperature between 14°–24° C. with an ice-water cooling batch. After addition, the mixture was aged at 18° to 20° C. for 30 minutes and checked by HPLC analysis for the disappearance of (−)-cis-1-aminoindan-2-ol.

Progress of the reaction is monitored by high performance liquid chromatography (HPLC) analysis: 25 cm Dupont C8-RX column, 60:40 acetonitrile/10 mM ($KH_2PO_4$/$K_2HPO_4$), 1.0 mL/min., injection volume=20 mL, detection=200 nm, sample preparation=500×dilution. Approximate retention times:

| retention time (min.) | identity |
|---|---|
| 6.3 | cis-aminoindanol |

The reaction was treated with pyridinium p-toluenesulfonate (241 g, 0.96 mol, 0.16 equiv.) and stirred for 10 minutes (the pH of the mixture after diluting 1 mL sample with an equal volume of water is between 4.3–4.6). Then, 2-methoxypropene (1.27 L, 13.24 mol, 2.2 equiv.) was added and reaction was heated to 38°–40° C. for 2 h. The reaction mixture was cooled to 20° C. and partitioned with ethyl acetate (12 L) and 5% aqueous $NaHCO_3$ (10 L). The mixture was agitated and the layers were separated. The ethyl acetate extract was washed with 5% aqueous $NaHCO_3$ (10 L) and water (4 L). The ethyl acetate extract was dried by atmospheric distillation and solvent switched to cyclohexane (total volume of~30L). At the end of the distillation and concentration (20 volume % of ethyl acetate extraction volume), the hot cyclohexane solution was allowed to slowly cool to 25° C. to crystallize the product. The resulting slurry was further cooled to 10° C. and aged for 1 h. The product was isolated by filtration and the wet cake was washed with cold (10° C.) cyclohexane (2×800 mL). The washed cake was dried under vacuum (26" of Hg) at 40° C. to afford 1.65 kg of acetonide 1 (86.4%, 98 area % by HPLC), 1H NMR (300.13 MHz, $CDCl_3$, major rotamer) δ7.36–7.14 (m, 9H), 5.03 (d, J=4.4, 1H), 4.66 (m, 1H) 3.15 (m, 2H), 3.06 (br s, 2H), 2.97 (m, 2H), 1.62 (s, 3H), 1.37 (s, 3H); $^{13}C$ NMR (75.5 MHz, $CDCl_3$, major rotamer) $δ_c$ 168.8, 140.9, 140.8, 140.6, 128.6, 128.5, 128.4, 127.1,126.3, 125.8, 124.1, 96.5, 78.6, 65.9, 38.4, 36.2, 31.9, 26.5, 24.1. Anal. Calcd for $C_{21}H_{23}NO_2$: C, 78.47; H, 7.21; N, 4.36. Found: C, 78.65; H, 7.24; N, 4.40.

EXAMPLE 2

Preparation of Epoxide 3
a. Tosylate Method

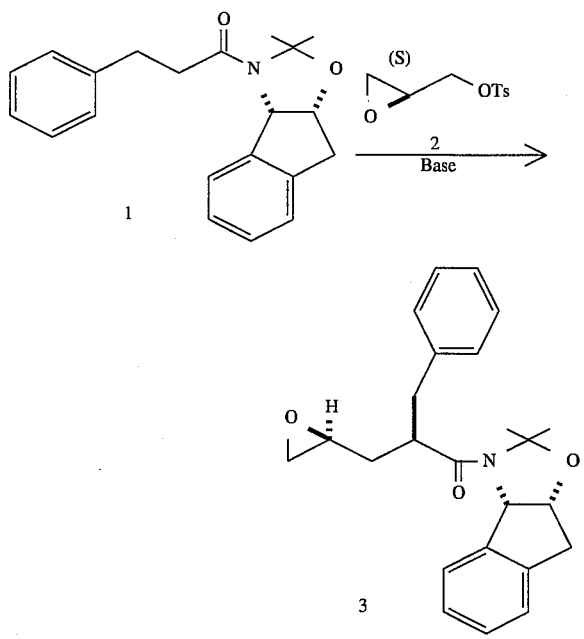

A solution of acetonide 1 (1000 g, 3.11 mol) and 2(S)-glycidyl tosylate 2 (853 g, 3.74 mol, 1.2 equiv.) in 15.6 L of THF (KF=22 mg/mL) in a 50 L 4-neck round bottom flask, equipped with a thermocouple, mechanical stirrer, addition funnel and nitrogen inlet adapter was degasseal 3 times via vacuum-nitrogen purge and cooled to −56° C. Then, lithim hexamethyldisilazide ($LiN[(CH_3)_3Si]_2$)(2.6 L, 1.38M, 1.15 equiv.) was added over 2 h, while keeping the internal temperature between −50° to −45° C. The reaction mixture was stirred at −45° to −40° C. for 1 h and then allowed to warm to −25° C. over 1 h. The mixture is stirred between −25° to −22° C. for 4 h (or until the starting acetonide is 3.0 area %).

Progress of the reaction is monitored by HPLC analysis: 25 cm×4.6 nm Zorbax Silica column, 20% ethyl acetate in hexane, 2.0 mL/min, injection volume=20 mL, detection= 254 nm, sample preparation=100×dilution. Approximate retention times:

| retention time (min.) | identity |
|---|---|
| 5.5 | amide 1 |
| 6.5 | glycidyl tosylate 2 |
| 13.5 | epoxide 3 |

The reaction mixture was quenched with DI water (6.7 L) at −15° C. and partitioned with ethyl acetate (10 L). The mixture was agitated and the layers were separated. The ethyl acetate extract was washed with a mixture of 1% aqueous $NaCHO_3$ (5 L) and saturated NaCl (0.5 L). The ethyl acetate extract (28.3 L) was concentrated by vacuum distillation (28" of Hg) and additional ethyl acetate was added to complete the solvent switch to ethyl acetate (final volume=11.7 L). The ethyl acetate concentrate was further solvent switched to MeOH to crystallize the product and concentrated to a final volume of 3.2 L. The residual ethyl acetate solvent was removed by charging 10 L of methanol and collecting 10 L of distillate. The resulting slurry was stirred at 22° C. for 1 h, then cooled to 5° C. and aged for 0.5 h. The product was isolated by filtration and the wet cake was washed with cold methanol (2×250 mL). The washed cake was dried under vacuum (26" of Hg) at 25° C. to afford 727 g of epoxide 3 (61.2%, 98.7 area % of the major epoxide by HPLC): $^{13}C$ NMR (300 MHz, $CDCl_3$) δ171.1,140.6, 140.5, 139.6, 129.6, 128.8, 128.2, 127.2, 126.8, 125.6, 124.1, 96.8, 79.2, 65.8, 50.0, 48.0, 44.8, 39.2, 37.4, 36.2, 26.6, 24.1.

b. Epichlorohydrin Method
Preparation of Epoxide 3 (epichlorohydrin method)

A solution of acetonide 1 (3.00 g, 9.33 mmol) in 47 mL of sieve dried THF was degassed with nitrogen and the resulting solution was cooled to −78° C. and treated with 8.0 mL of lithium hexamethyldisilylazide solution (1.38M in THF). The resulting solution was aged at −78° C. for 15 min., then 2(S)-epichlorohydrin (1.2 mL, 15.3 mmol) was added dropwise, and the resulting mixture was allowed to warm to −25° C. over 1 h and aged for 1 h. The reaction mixture was then recooled to −78° C. and treated with 3.0 mL of lithium hexamethyldisilylazide solution, followed by 1.0 mL of (S)-epichlorohydrin. The reaction mixture was allowed to warm to −25° C. and aged for 2 h. The reaction mixture was quenched with 20 mL of saturated aqueous sodium bicarbonate and extracted with 120 mL of EtOAc, and back-extracted with 60 mL of EtOAc. The combined organic phase was washed with brine, dried ($MgSO_4$), filtered and concentrated at reduced pressure to afford 3.97 g of an oil that was purified by silica gel chromatography (80 g $SiO_2$, elution with 4:1 hexane/ethyl acetate) to afford 2.9 g of a mixture of the desired epoxide 3 and the intermediate chlorohydrin product. A portion of the mixture (1.29 g) was dissolved in sieve dried THF (20 mL) at 25° C. and treated with 1.73 g of 25 wt. % solution of potassium t-amylate and the mixture was aged at 25° C. for 1 h. The reaction mixture was partitioned between ethyl acetate and saturated sodium bicarbonate and the layers were separated. The organic phase was washed with brine, dried ($MgSO_4$) and concentrated at reduced pressure to an oil. The oil was purified by silica gel chromatography (80 g $SiO_2$, elution with 4:1 hexane/ethyl acetate) to afford 1.1 g (70% overall) of the epoxide 3.

EXAMPLE 3

Preparation of penultimate 6

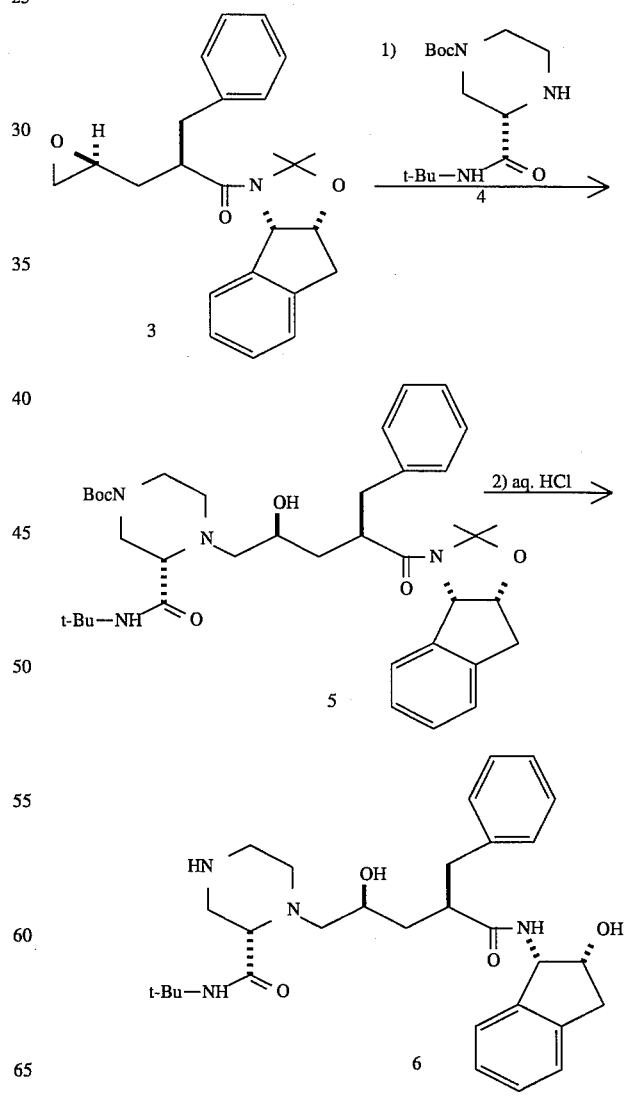

A slurry of the 2(S)-t-butylcarboxamide-4-N-Bocpiperazine 4 (1950 g, 6.83 mol, >99.5% ee) (ee=enantiomeric excess) and the epoxide 3 (2456 g, 97.5:2.5 mixture of 4S/R epoxides, 6.51 mol) in isopropanol (2-propanol, 18.6 L) in a 72 L round bottom flask with four inlets, equipped with a mechanical stirrer, reflux condenser, steam bath, Teflon coated thermocouple and nitrogen inlet, was heated to reflux (internal temperature was 84°–85° C.). After 40 min, a homogeneous solution was obtained. The mixture was heated at reflux for 28 h.

The internal temperature during reflux was 84°–85° C. Progress of the reaction was monitored by HPLC analysis: 25 cm Dupont C8-RX column, 60:40 acetonitrile/10 mM (KH$_2$PO4/K$_2$HPO$_4$), 1.0 mL/min., detection=220 nm, sample preparation=2 μL, reaction mixture diluted to 1 mL in acetonitrile. Approximate retention times:

| retention time (min) | identity |
|---|---|
| 4.8 | piperazine 4 |
| 8.9 | epoxide 3 |
| 15.2 | coupled product 5 |

After 28 h, the remaining epoxide 3 and coupled product 5 (by HPLC analysis) were 1.5 area % and 91–93 area %, respectively. The mixture was cooled to 0° to 5° C. and 20.9 L of 6N HCl was added while keeping the temperature below 15° C. After the addition was complete, the mixture was warmed to 22° C. Evolution of gas is noted at this point (isobutylene). The mixture was aged at 20° to 22° C. for 6 h.

Progress of the reaction was monitored by HPLC analysis: same conditions as above. Approximate retention times:

| retention time (min) | identity |
|---|---|
| 7.0 | cis-aminoindanol |
| 11.9 | penultimate 6 |
| 15.1 | coupled product 5 |

The mixture was cooled to 0° C. and 7.5 L of 50% NaOH was slowly added to adjust the pH of the mixture to pH=11.6, while keeping the temperature less than 25° C. during the addition. The mixture was partitioned with ethyl acetate (40 L) and water (3 L). The mixture was agitated and the layers were separated. The organic phase (60 L) was concentrated under reduced pressure (29" of Hg) and solvent switched to DMF and concentrated to a final volume of 10.5 L (KF= 1.8 mg/mL). The HPLC assay yield of 6 in ethyl acetate was 86.5%. The penultimate compound 6 in DMF was directly used in the next step without further purification. For isolated 6: $^{13}$C NMR (75.4 MHz, CDCl$_3$) δ175.2, 170.5, 140.8, 140.5, 139.9, 129.1, 128.5, 127.9, 126.8, 126.5, 125.2, 124.2, 73.0, 66.0, 64.8, 62.2, 57.5, 49.5, 47.9, 46.4, 45.3, 39.6, 39.3, 38.2, 28.9.

EXAMPLE 4

Preparation of L-735,524-monohydrate

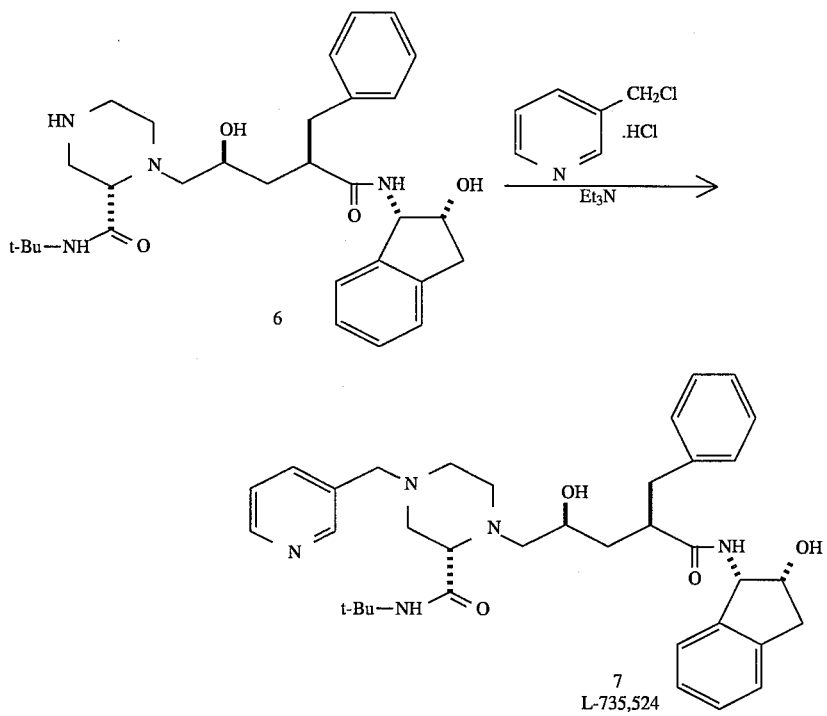

The solution of 6 in DMF (10.5 L, KF=10 mg/mL) from the previous step was charged with 8 L of sieve dried DMF (KF.<30 mg/L) and the mixture was heated with a steam bath under vacuum of 30" of Hg to distill off mainly water and/or any residual isopropanol or ethyl acetate solvent. The final concentrate volume was 13.5 L (KF=1.8 mg/mL) and then triethylamine (2.86 L, 20.51 tool) was added to the 25° C. solution followed by 3-picolyl chloride hydrochloride (96%, 1287 g, 7.84 tool). The resulting slurry was heated to 68° C.

The progress of the reaction was followed by HPLC analysis using the same conditions as the previous step. Approximate retention times:

| Retention time (min) | Identity |
| --- | --- |
| 2.7 | DMF |
| 4.2 | 3-picolyl chloride |
| 4.8 | L-735,524 |
| 9.1 | penultimate 6 |

The mixture was aged at 68° C. until the residual penultimate compound 6 was <0.3 area % by HPLC analysis.

The mixture was stirred at 68° C. for 4 h, then cooled to 25° C. and partitioned with ethyl acetate (80 L) and a mixture of 24 L of saturated aqueous $NaCHO_3$ and distilled war (14 L). The mixture was agitated at 55° C. and the layers were separated. The ethyl acetate layer was washed three times with water (20 L) at 55° C. The washed ethyl acetate layer is concentrated at atmospheric pressure to a final pot volume of 30 L. At the end of the atmospheric concentration, water (560 mL) was added to the hot solution and the mixture was cooled to 55° C. and seeded with L-735,524 monohydrate. The mixture was cooled to 4° C. and filtered to collect the product. The product was washed with cold ethyl acetate (2×3 L), and dried at house vacuum at 25° C. to afford 2905 g (70.7%) of L-735,524 monohydrate as a white solid.

EXAMPLE 5

Pyrazine-2-tert-butyl carboxamide 9

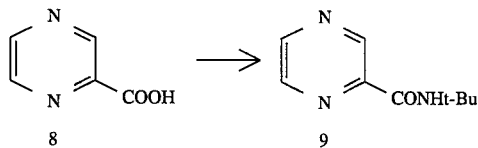

| 2-Pyrazinecarboxylic acid (8) | 3.35 kg (27 mol) |
| --- | --- |
| Oxalyl chloride | 3.46 kg (27.2 mol) |
| tert-Butylamine (KF = 460 µg/ml) | 9.36 L (89 mol) |
| EtOAc (KF = 56 µg/ml) | 27 L |
| DMF | 120 mL |
| 1-Propanol | 30 L |

The carboxylic acid 8 was suspended in 27 L of EtOAc and 120 mL of DMF in a 72 L 3-neck flask with mechanical stirring under $N_2$ and the suspension was cooled to 2° C. The oxalyl chloride was added, maintaining the temperature between 5° and 8° C.

The addition was completed in 5 h. During the exothermic addition CO and $CO_2$ were evolved. The HCl that was formed remained largely in solution. A precipitate was present which is probably the HCL salt of the pyrazine acid chloride. Assay of the acid chloride formation was carried out by quenching an anhydrous sample of the reaction with t-butylamine. At completion <0.7% of acid 8 remained.

The assay for completion of the acid chloride formation is important because incomplete reaction leads to formation of a bis-tert-butyl oxamide impurity.

The reaction can be monitored by HPLC: 25 cm Dupont Zorbax RXC8 column with 1 mL/min flow and detection at 250 nm; linear gradient from 98% of 0.1% aqueous $H_3PO_4$ and 2% $CH_3CN$ to 50% aqueous $H_3PO_4$ and 50% $CH_3CN$ at 30 min. Retention times: acid 8=10.7 min, amide 9=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated tert-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% $NaCHO_3$ and 2×2 L of saturated aq. NACl. The organic phase was treated with 200 g of Darco G60 carbon and filtered through Solka Flok and the cake was washed with 4 L of EtOAc.

Carbon treatment efficiently removed some purple color in the product.

The EtOAc solution of 9 was concentrated at 10 mbar to 25% of the original volume. 30 L of 1-propanol were added, and the distillation was continued until a final volume of 20 L was reached.

At this point, the EtOAc was below the limit of detection in the $^1H$ NMR (<1%). The internal temperature in this solvent change was <30° C. A 1-propanol/EtOAC solution of 3 was stable to reflux at atmospheric pressure for several days.

Evaporation of an aliquot gave a tan solid m.p 87°–88° C. $^{13}C$ NMR (75 MHz, $CDCl_3$, ppm) 161.8, 146.8, 145.0, 143.8, 142.1, 51.0, 28.5.

EXAMPLE 6 rac-2-tert-Butyl-carboxamide-piperozine 10

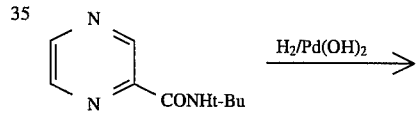

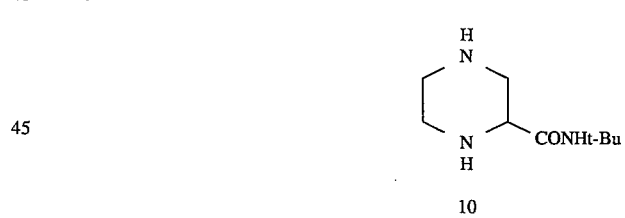

Materials

Pyrazine-2-tert-butylcarboxamide 9 2.4 kg (13.4 mol) in 1-Propanol solution 12 L 20% $Pd(OH)_2$/C16 wt. % water 144 g The pyrazine-2-tert-butylcarboxamide 9/1-propanol solution was placed into the 5 gal autoclave. The catalyst was added and the mixture was hydrogenated at 65° C. at 40 psi (3 atm) of $H_2$.

After 24 h. the reaction had taken up the theoretical amount of hydrogen and GC indicated <1% of 9. The mixture was cooled, purged with $N_2$ and the catalyst was removed by filtration through Solka Floe. The catalyst was washed with 2 L of warm 1-propanol.

It was found that the use of warm 1-propanol during washing of the filter cake improved filtration and lowered the losses of product on the filter cake.

The reaction was monitored by GC: 30 m Megabore column, from 100° C. to 160° C. at 10° C./min, hold 5 min, then at 10° C./min to 250° C., retention times: 9=7.0 min, 10=9.4 min. The reaction could also be monitored by TLC with EtOAc/MeOH (50:50) as solvent and Ninhydrin as developing agent.

Evaporation of an aliquot indicated that the yield over amidation and hydrogenation is 88% and that the concentration of 10 is 133 g/L.

Evaporation of an aliquot gave 10 as a white solid m.p. 150°–151° C.; $^{13}$C NMR (75 MHz, D$_2$O, ppm) 173.5, 59.8, 52.0, 48.7, 45.0, 44.8, 28.7.

EXAMPLE 7

(S)-2-tert-Butyl-carboxamide-piperazine bis (S)-Camphorsulfonic acid salt (S)-11

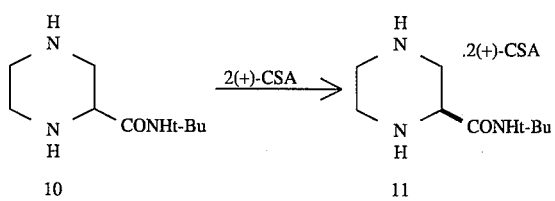

| Materials | |
|---|---|
| rac-2-tert-Butyl-carboxamide-piperazine 10 in 1-Propanol Solution | 4.10 kg (22.12 mol) in 25.5 Kg solvent |
| (S)-(+)-10-Camphorsulfonic acid | 10.0 Kg (43.2 mol) |
| 1-Propanol | 12 L |
| Acetonitrile | 39 L |
| Water | 2.4 L |

The solution of amine 10 in 1-propanol was charged to a 100 L flask with an attached batch concentrator. The solution was concentrated at 10 mbar and a temperature <25° C. to a volume of ca 12 L.

At this point the product had precipitated from the solution, but went back into a solution when the mixture was heated to 50° C.

Analysis of a homogeneous aliquot indicated that the concentration of 10 was 341 g/L The concentration was determined by HPLC: 25 cm Dupont Zorbax RXC8 column with 1.5 mL/min flow and detection at 210 nm, isocratic (98/2) CH$_3$CN/0.1% aqueous H$_3$PO$_4$. Retention time of 10: 2.5 min.

Acetonitrile (39 L) and water (2.4 L) were added to give a clear, slightly brown solution.

Determination of the water content by KF titration and CH$_3$CN/1-propanol ratio by $^1$H NMR integration showed that the CH3CN/1-propanol/H$_2$O ratio was 26/8/1.6. The concentration in the solution was 72.2 g/L.

The (S)-10-camphorsulfonic acid was charged over 30 min in 4 portions at 20° C. The temperature rose to 40° C. after the CSA was added. After a few minutes a thick white precipitate formed. The white slurry was heated to 76° C. to dissolve all the solids, the slightly brown solution was then allowed to cool to 21° C. over 8 h.

The product precipitated at 62° C. The product was filtered without aging at 21° C., and the filter cake was washed with 5 L of the CH$_3$CN / 1-propanol / H$_2$O 26/8/1.6 solvent mixture. It was dried at 35° C. in the vacuum oven with N$_2$ bleed to give 5.6 Kg (39%) of 11 as a white crystalline solid m.p 288°–290° C. (with decomp.) [α]D$^{25}$= 18.9° (c=0.37, H$_2$O). $^{13}$C NMR (75 MHz, D$_2$O, ppm) 222.0, 164.0, 59.3, 54.9, 53.3, 49.0, 48.1, 43.6, 43.5, 43.1, 40.6, 40.4, 28.5, 27.2, 25.4, 19.9, 19.8.

The ee of the material was 95% according to the following chiral HPLC assay: an aliquot of 11 (33 mg) was suspended in 4 mL of EtOH and 1 mL of Et$_3$N. Boc$_2$O (11 mg) was added and the reaction mixture was allowed to age for 1 h. The solvent was completely removed in vacuo, and the residue was dissolved in ca. 1 mL of EtOAc and filtered through a Pasteur pipet with SiO$_2$, using EtOAc as eluent. The evaporated product fractions were redissolved in hexanes at ca. 1 mg/mL. The enantiomers were separated on a Daicel Chiracell AS column with a hexane/IPA (97:3) solvent system at a flow rate of 1 mL/min and detection at 228 nm. Retention times: S antipode=7.4 min, R=9.7 min.

EXAMPLE 8

(S)-2-tert-Butylcarboxamide-4-tert-butoxycarbonyl-piperazine 4 from salt 11

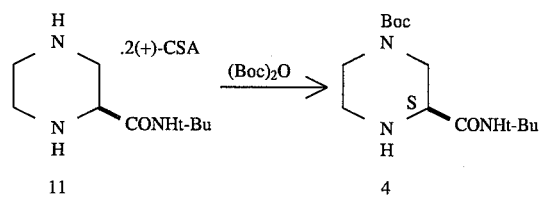

| Materials | |
|---|---|
| (S)-2-tert-Butyl-carboxamide-piperazine Bis (S)-(+)-CSA salt 11, 95% ee | 5.54 Kg (8.53 mol) |
| Di-tert-butyl dicarbonate | 1.86 Kg (8.53 mol) |
| Et$_3$N | 5.95 L (42.6 mol) |
| EtOH Punctilious 200 proof | 55 L |
| EtOAc | 2 L |

To the (S)-CSA salt 11 in a 100 L 3-neck flask with an addition funnel under N$_2$ was added EtOH, followed by triethylamine at 25° C. The solid dissolved readily on the addition of the Et$_3$N. The Boc$_2$O was dissolved in EtOAc and charged to the addition funnel. The solution of Boc$_2$O in EtOAc was added at such a rate as to keep the temperature below 25° C. The addition took 3 h. The reaction mixture was aged for 1 h after completion of the addition of the Boc$_2$O solution.

The reaction can be monitored by HPLC: 25 cm Dupont Zorbax RXC8 column with 1 mL/min flow and detection at 228 nm, isocratic (50/50) CH$_3$CN/0.1M KH$_2$PO$_4$ adjusted to pH=6.8 with NaOH. Retention time of 4=7.2 min. The chiral assay was carried out using the same system as in the previous step. The reaction could also be monitored by TLC with a 100% EtOAc as the solvent. (Rf=0.7)

The solution was then concentrated to ca. 10 L at an internal temperature of <20° C. in a batch-type concentrator under 10 mbar vacuum. The solvent switch was completed by slowly bleeding in 20 L of EtOAc and reconcentrating to ca 10 L. The reaction mixture was washed into an extractor with 60 L of EtOAc. The organic phase was washed with 16 L of 5% aqueous Na$_2$CO$_3$ solution, 2×10 L Di water and 2×6 L of saturated aqueous sodium chloride. The combined aqueous washes were back extracted with 20 L of EtOAc and the organic phase was washed with 2×L water and 2×4 L of saturated aqueous sodium chloride. The combined EtOAc extracts were concentrated under 10 mbar vacuum with an internal temperature of <20° C. in a 100 L batch-type concentrator to ca. 8 L. The solvent switch to cyclohexane was achieved by slowly bleeding in ca. 20 L of cyclohexane, and reconcentrating to ca. 8 L. To the slurry was added 5 L of cyclohexane and 280 mL of EtOAc and the mixture was heated to reflux, when everything went into solution. The solution was cooled and seed (10 g) was added at 58° C. The slurry was cooled to 22° C. in 4 h and the product was isolated by filtration after a 1 h age at 22° C. The filter cake was washed with 1.8 L of cyclohexane and dried in the vacuum oven at 35° C. under $N_2$ bleed to give 1.87 Kg (77%, >99.9 area % by HPLC, R-isomer below level of detection) of 4 as a slightly tan powder. $[\alpha]D^{25}=22.0°$ (c=0.20, MeOH), m.p 107° C.; $^{13}C$ NMR (75 MHz, $CDCl_3$, ppm) 170.1, 154.5, 79.8, 58.7, 50.6, 46.6, 43.6, 43.4, 28.6, 28.3.

EXAMPLE 9

(S)-2-tert-Butyl-carboxamide-piperazine bis (L)-Pyroglutamic acid 12

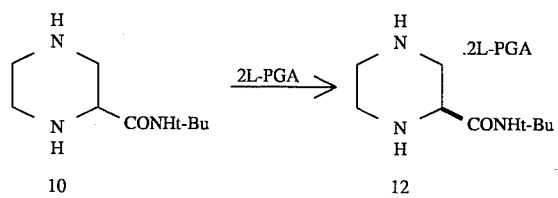

| Materials | |
|---|---|
| rac-2-tert-butyl-carboxamide-piperazine 10 in 1-propanol solution | (0.11 mol) 155 ml, assay = 21.1 g |
| L-pyroglutamic acid | 28 g, (0.21 mol) |
| Water | 5 ml |

The solution of racemic-2-tert-Butyl-carboxamide-piperazine 10 in 1-propanol was charged to a 500 ml round bottom flask with a reflux condenser, mechanical stirrer and a nitrogen inlet. Water was added along with L-pyroglutamic acid and the resulting slurry was heated to reflux. The homogeneous yellow solution was cooled to 50° C. and seeded with the bis-(L)-PGA salt of the R amine (50 nags). Solids began forming immediately. The solution was further cooled to 25° C. and aged for 16 hours. The solids were filtered at 22° C., and the filter cake was washed with 35 ml cold 1-propanol/1% water. The filter cake was dried at 35° C. in the vacuum oven with $N_2$ bleed to give 23.74 gms (48%) of (R)-2-tert-Butyl-carboxamide-piperazine bis (L)-Pyroglutamic acid. The ee of the material was 98% according to the chiral HPLC assay described previously. The yellow mother liquors contained 22.6 gms (46%) of (S)-2-tert-Butyl-carboxamide-piperazine bis (L)-Pyroglutamic acid salt 12 and the ee was 95% according to the chiral HPLC assay. The mother liquors were evaporated and used directly in the protection step.

EXAMPLE 10

(S)-2-tert-Butylcarboxamide-4-tert-butoxycarbonyl-piperazine 4 from (S)-2-tert-Butyl-carboxamide-piperazine bis (L)-pyroghtamic acid salt 12

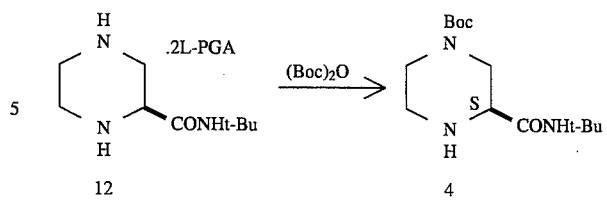

| Materials | |
|---|---|
| (S)-2-tert-Butyl-carboxamide-piperazine Bis (L)-pyroglutamic acid salt, 95% ee | 22.6 g (50.1 mmol) |
| Di-tert-butyl dicarbonate | 11.1 g (50.1 mmol) |
| $Et_3N$ | 35.5 mL (0.254 mol) |
| 1-Propanol | 226 ml |
| EtOAc | 24 ml |

To (S)-2-tert-butyl-carboxamide-piperazine bis (L)-pyroglutamic acid salt in a 500 ml 3-neck flask with addition funnel under $N_2$ was added 1-propanol. The gummy yellow solid dissolved readily on the addition of the $Et_3N$. A solution of $Boc_2O$ in EtOAc was added over 2 h at 22° C. The reaction mixture was aged for 1 h after completion of the addition.

The reaction could be monitored by HPLC and TLC using the same procedures as for the conversion of 11 to 4

The solution was then concentrated and solvent switched to ethyl acetate (200 ml). The reaction mixture was washed with 50 ml of 7% aqueous $Na_2CO_3$ solution, 2×30 ml water and dried ($Na_2SO_4$) and filtered. The EtOAc solution was concentrated and solvent switched to cyclohexane (60 ml). EtOAc (1 mL) was added and the mixture was heated to reflux to dissolve all solids. The mixture was cooled and seeded (50 mg) at 52° C. The slurry was cooled to 22° C. over 2 h and the product was isolated by filtration after a 1 h age at 22° C. The filter cake was washed with 8 ml of cyclohexane and dried in the vacuum oven at 35° C. under $N_2$ bleed to give 10.8 gms (74%).(>99.9 area % by HPLC analysis, R-isomer below level of detection) of 4 as an off white powder.

EXAMPLE 11

Kinetic Resolution of (S/R)-2-tert-Butylcarboxamide-4-tert-butoxycarbonyl-piperazine 13 to 4

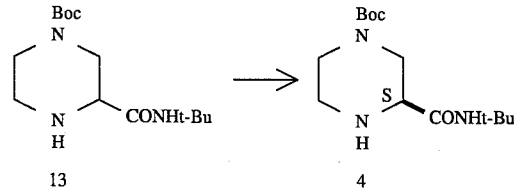

| Materials | |
|---|---|
| Crude (S/R)-2-tert-Butylcarboxamide-4-tert-butoxy-carbonyl-piperazine 13 | 1.40 g |
| (S)-2-tert-Butylcarboxamide-4-tert-butoxycarbonyl-piperazine 4 (>99.5% ee) | 4 × 0.14 g |
| Methylcyclohexane with 2% (vol/vol) EtOAc | 14 mL |

The crude, gummy 13 is dissolved in 14 mL of the solvent mixture by heating to 90° C. The solution is allowed to cool, and at 10° C. intervals the solution is seeded with 0.14 g of 4 (>99.5% ee). At 55° C. the fourth 0.14 g batch of seed does not dissolve any more and on further slow cooling to room temperature a white crystalline mass forms. The reaction mixture is filtered, washed with 3 mL of the methylcyclohexane/EtOAc solvent mixture and dried in the vacuum oven under $N_2$ bleed to give 0.95 g of a white solid. Determination of the enantiomeric purity with a Chiracell AS column shows 93%ee.

EXAMPLE 12

Preparation of trans-3-(4-pyridyl)acrylic acid

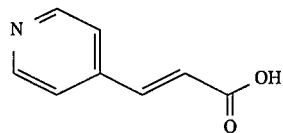

To a solution of 4-pyridine carboxaldehyde (36.7 mL, 0.384 mol) and malonic acid (40 g, 0.384 mol) in 31 mL of pyridine was added piperdine (0.12 mL) and the mixture was warmed to 100° C. Caution: large volumes of $CO_2$ evolved. After 0.5 h, the reaction was cooled to room temperature (RT) and the solution solidified. This was triturated with 240 mL of water and filtered, and washed with 2×50 mL portions of water. The solid was dried overnight at 42° C. under vacuum (10 mm Hg) to provide 37.1 g of a white solid; mp 295°–297° C.

EXAMPLE 13

Preparation of N-(2(R)-hydroxy-1(S)-indanyl)-trans-3-(4-pyridyl) acrylamide

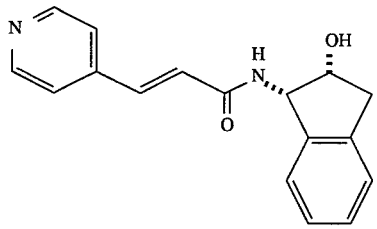

To a suspension of trans-3-(4-pyridyl)acrylic acid (10.0 g, 0.067 mol) in 500 mL of THF was added triethylamine (10.29 mL, 0.0738 mol) and the solution was cooled to 0° C. Trimethylacetyl chloride (8.68 mL, 0.0704 mol) was added and the reaction stirred for 0.5 h. 2(R)-hydroxy-1(S)-indane (10.0 g, 0.067 mol) dissolved in 260 mL of THF was added via cannula. After 2 h the reaction was warmed to RT and stirred an additional 15 h. The solvent was removed in vacuo and the resulting solid was triturated with cold ethyl acetate (150 mL) and filtered. This was dried overnight under vacuum (0.5 mm of Hg) to provide 18.5 g of a white solid; mp 205°–207° C.

EXAMPLE 14

Preparation of N-(1,2-N,O-isopropylidenen-2(R)-hydroxy-1(S)-indanyl)-trans-3-(4-pyridyl)acrylamid

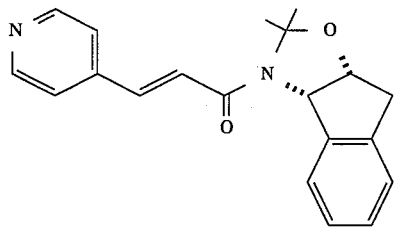

To a suspension of N-(2(R)-hydroxy-1(S)-indanyl)-trans-3-(4-pyridyl) acrylamide (18.5 g, 0.066 mol) in 700 mL of methylene chloride was added dimethoxypropane (49.0 mL, 0.402 mol) followed by (+/−) camphor sulphonic acid (46.8 g, 0.201 mol). After 20 minutes the reaction became homogeneous. The reaction mixture stirred for 3 h and was washed with saturated $NaCHO_3$ (2×150 mL). The aqueous layer was extracted with methylene chloride (3×200 mL) and the combined organic layer was dried over $MgSO_4$, filtered and concentrated to an oil. Purification by flash column chromatography (100×150 mm column of silica gel; gradient elution 1:30:69, 2:30:68, 3:30:67, 5:30:65 MeOH:$CHCl_3$ saturated with $NH_3$: $CH_2Cl_2$) provided 16.0 g of a white foam. (Rf 0.46 in 5:30:65 MeOH:$CHCl_3$ saturated with $NH_3$: $CH_2Cl_2$)

EXAMPLE 15

Preparation of N-(1,2-N,O-isopropylidenen-2(R)-hydroxy-1(S)-indanyl)-3-(4-pyridyl)propylamide

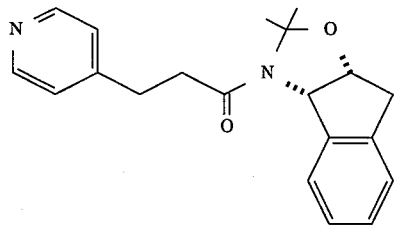

To N-(1,2-N,O-isopropylidenen-2(R)-hydroxy-1(S)-indanyl)-trans-3-(4-pyridyl)acrylamide (16.0 g, 0.0499 mol) dissolved in ethanol (200 mL) and THF (200 mL) was added 14.0 g Pd(OH)$_2$ on is carbon (20% by weight). The flask was then charged with $H_2$ and stirred 9 h. The solution was purged with Ar, filtered through a plug of celite and washed with ethanol (100 mL). The solvent was removed in vacuo and the product was purified via flash column chromatography (100×150 mm column of silica gel; gradient elution 1:30:69, 2:30:68, 3:30:67, 5:30:65 MeOH:$CHCl_3$ saturated with $NH_3$: $CH_2Cl_2$) which provided 13.8 g of a white foam. (Rf 0.5 in 5:30:65 MeOH:$CHCl_3$ saturated with $NH_3$: $CH_2Cl_2$)

EXAMPLE 16

Preparation of N-(2(R)-hydroxy- 1(S)-indanyl)-trans-3-(3-pyridyl) acrylamide

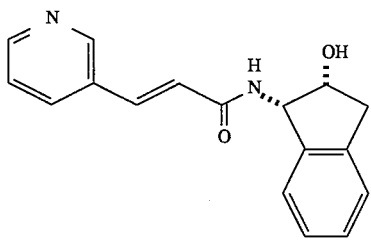

Using substantially the same procedure as for the preparation of N-(2(R)-hydroxy-1(S)-indanyl)-trans-3-(4-pyridyl)acrylamide, but substituting the appropriate starting materials, the title compound was prepared. Physical data: mp 119–120, Analysis Calculated for $C_{17}H_{16}N_2O_2 \cdot 0.65H_2O$: C, 69.92; H, 5.97; N, 9.59. Found: C, 69.94; H, 5.74, N, 9.84.

EXAMPLE 17

Preparation of N-(1,2-N,O-isopropylidenen-2(R)-hydroxy-1(S)-indanyl)-trans-3-(3-pyridyl)acrylamide

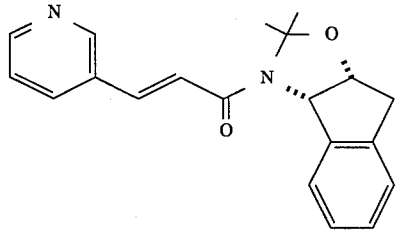

Using substantially the same procedure as for the preparation of N-(1,2-N, O-isopropylidenen-2(R )-hydroxy-1(S)-indanyl)-trans-3-(4-pyridyl)acrylamide, but substituting the appropriate starting material, the title compound was prepared. Physical data: mp 134–136, Analysis Calculated for $C_{20}H_{20}N_2O_2 \cdot 0.25H_2O$: C, 73.94; H, 6.36; N, 8.62. Found: C, 73.95; H, 6.18, N, 8.70.

EXAMPLE 18

Preparation of N-(1,2-N,O-isopropylidenen-2(R )-hydroxy-1(S)-indanyl)- 3-(3-pyridyl)propylamide

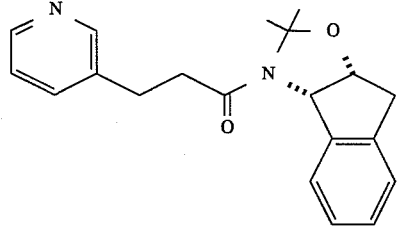

Using substantially the same procedure as for the preparation of N-(1,2-N,O-isopropylidenen-2(R)-hydroxy-1(S)-indanyl)-3-(4-pyfidyl)propylamide, but substituting the appropriate starting material, the title compound was prepared.

While the foregoing specification teaches the principles of the present invention, with examples provided for the purpose of illustration, it will be understood that the practice of the invention encompasses all of the usual variations, adaptations, and modifications, as come within the scope of the following claims and its equivalents.

What is claimed is:

1. A process for making a compound of formula I

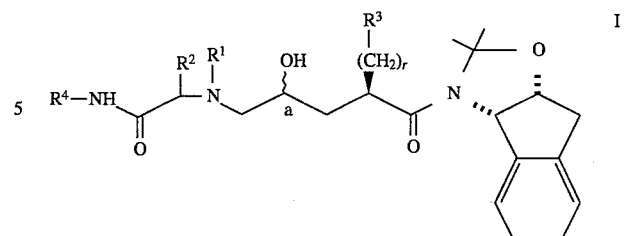

comprising reacting a compound of formula IV

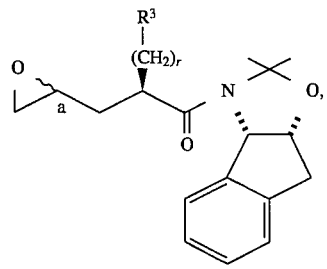

with an amine of formula V

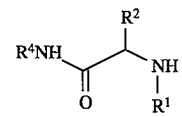

wherein:

stereocenter a is in either the R configuration, the S configuration or is racemic;

r is an integer from zero through and including 5;

$R^1$ and $R^2$ are independently selected at each occurrence from the group consisting of:
1) hydrogen,
2) —$C_{1-4}$ alkyl unsubstituted or substituted with one or more of
   a) hydroxy,
   b) $C_{1-3}$ alkoxy,
   c) aryl unsubstituted or substituted with one or more of $C_{1-4}$alkyl, hydroxy or aryl,
   d) —W-aryl or —W-benzyl, wherein W is —O—, or —S—,
   e) a 5–7 membered cycloalkyl group unsubstituted or substituted with one or more of
      i) hydroxy,
      ii) $C_{1-3}$ alkoxy, or
      iii) aryl,
   f) heterocycle unsubstituted or substituted with one or more of hydroxy, $C_{1-4}$alkyl, $C_{1-4}$alkyl substituted with hydroxy, or Boc,
   g) —NH—COO$C_{1-3}$alkyl,
   h) —NH—CO—$C_{1-3}$alkyl,
   i) —NH—SO$_2C_{1-3}$alkyl,
   j) —COOR, or
   k) —(($CH_2)_mO)_nR$, or
3) aryl, unsubstituted or substituted with one or more of
   a) halo,
   b) hydroxy,
   c) —$NO_2$ or —$N(R)_2$,
   d) $C_{1-4}$alkyl,
   e) $C_{1-3}$ alkoxy, unsubstituted or substituted with one or more of —OH or $C_{1-3}$ alkoxy,
   f) —COOR,
   g) —$CON(R)_2$,
   h) —$CH_2N(R)_2$,
   i) —$CH_2NHCOR$, j) —CN,
k) —CF$_3$,
l) —NHCOR,
m) aryl C$_{1-3}$ alkoxy,
n) aryl,
o) —NRSO$_2$R,
p) —OP(O)(OR$_x$)$_2$, or
q) —R$^5$, as defined below; or R$^1$ and R$^2$ can be joined together with the nitrogen to which R$^1$ is attached and the carbon to which R$^2$ is attached to form a 3 to 10 membered monocyclic or bicyclic saturated ring system which consists of the nitrogen to which R$^1$ is attached and from 2 to 9 carbon atoms and is unsubstituted or substituted with one or more of:
1) hydroxy,
2) C$_{1-4}$ alkyl unsubstituted or substituted with one or more of
 a) halo,
 b) hydroxy,
 c) C$_{1-3}$ alkoxy,
 d) aryl,
 e) a 5–7 membered cycloalkyl group unsubstituted or substituted with one or more of
  i) hydroxy,
  ii) C$_{1-3}$ alkoxy, or
  iii) aryl, or
 f) heterocycle,
3) C$_{1-3}$ alkoxy,
4) —NH—COOC$_{1-3}$alkyl,
5) —NH—CO—C$_{1-3}$alkyl,
6) —NH—SO$_2$C$_{1-3}$alkyl,
7) heterocycle,
8) —W-aryl, or
9) —W—CO-aryl, wherein W is defined above; or R$^1$ and R$^2$ can be joined together with the nitrogen to which R$^1$ is attached and the carbon to which R$^2$ is attached to form a 3 to 10 membered monocyclic or bicyclic saturated ring system which consists of the nitrogen to which R$^1$ is attached, from 1 to 8 carbon atoms and one or more unsubstituted or substituted heteroatom selected from 1) 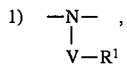

wherein V is absent or —CO—Q— or —SO$_2$—Q—,
R$^1$ is defined as above for when R$^1$ is independent from and not joined to R$^2$,
and wherein Q is absent or —O—, —N(R)—, or heterocycle optionally substituted with —C$_{1-4}$alkyl, 2) 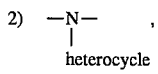

3) 

4) 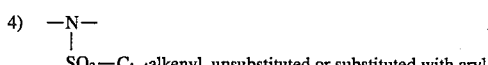

5) 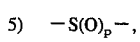

where in p is zero, 1 or 2, or

6) 

R$^3$ is selected from the group consisting of:
1) hydrogen,
2) —C$_{1-4}$ alkyl 3) C$_5$–C$_{10}$ cycloalkyl, optionally substituted with hydroxy,
4) C$_6$–C$_{10}$ aryl, unsubstituted or substituted with one or more of:
 a) halo,
 b) hydroxy,
 c) —NO$_2$ or —N(R)$_2$,
 d) C$_{1-4}$ alkyl,
 e) C$_{1-3}$ alkoxy, unsubstituted or substituted with one or more of —OH or C$_{1-3}$ alkoxy,
 f) —COOR,
 g) —CON(R)$_2$,
 h) —CH$_2$N(R)$_2$,
 i) —CH$_2$NHCOR,
 j) —CN,
 k) —CF$_3$,
 l) —NHCOR,
 m) aryl C$_{1-3}$ alkoxy,
 n) aryl,
 o) —NRSO$_2$R,
 p) —OP(O)(OR$_x$)$_2$, or
 q) —R$^5$, as defined below, or
5) monocyclic or bicyclic heterocycle containing from 1 to 3 heteroatoms chosen from the group consisting of N, O, and S, and which is unsubstituted or substituted with R$^5$ and optionally with one or more of
 a) halo,
 b) C$_{1-4}$ alkyl, or
 c) C$_{1-3}$ alkoxy;

m is 2, 3, 4 or 5;

n is zero, 1, 2 or 3;

R is hydrogen or C$_{1-4}$ alkyl;

R$_x$ is H or aryl;

R$^4$ is C$_{1-5}$ alkyl, straight or branched chain; and

R$^5$ is
1) —W—(CH$_2$)$_m$—NR$^6$R$^7$ wherein W and m are defined above, and R$^6$ and R$^7$ are independently selected at each occurrence from:
 a) hydrogen,
 b) C$_{1-6}$ alkyl, unsubstituted or substituted with one or more of
  i) C$_{1-3}$ alkoxy,
  ii) —OH, or
  iii) —N(R)$_2$,
 c) aromatic heterocycle unsubstituted or substituted with one or more of
  i) C$_{1-4}$ alkyl, or
  ii) —N(R)$_2$,
 d) or R$^6$ and R$^7$ are joined together with the nitrogen to which they are attached to form a 5–7 member heterocycle containing up to two additional heteroatoms selected from —N(R), —O—, —S—, —S(O)— or —S(0)$_2$—, the heterocycle optionally substituted with C$_{1-4}$ alkyl,
2) —(CH$_2$)$_q$—NR$^6$R$^7$ wherein q is an integer from 1–5, and R$^6$ and R$^7$ are defined above, except that R$^6$ or R$^7$ are not H or unsubstituted C$_{1-6}$ alkyl, or
3) benzofuryl, indolyl, azacycloalkyl, azabicyclo C$_{7-11}$ cycloalkyl, or benzopiperidinyl, unsubstituted or substituted with C$_{1-4}$ alkyl.

2. The process of claim 1 wherein the reaction is run in a solvent selected from a C$_{1-3}$ alcohol, and the temperature is from about 80° C. to 90° C.

3. The process of claim 2 wherein the solvent is isopropanol, and the temperature is from about 83° C. to 85° C.

4. The process of claim 1 further comprising the step of producing the compound of formula IV by reacting either a) a compound of formula II

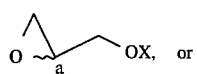      II or b) epichlorohydrin of the structure

with an amide of formula III

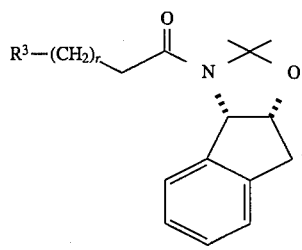      III in the presence of a strong base at low temperature, wherein X is selected from the group consisting of -H, methanesulfonyl, trifluoromethanesulfonyl, p-toluenesulfonyl, benzenesulfonyl, and 3-nitrobenzenesulfonyl.

5. The process of claim 4 wherein X is p-toluenesulfonyl.

6. The process of claim 1 wherein the stereocenter a is in the S configuration; r is 1; $R^1$ and $R^2$ are joined together to form a cyclic structure selected from the group consisting of:

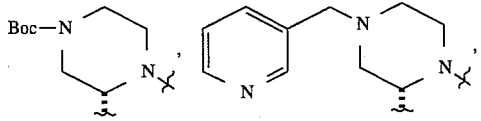

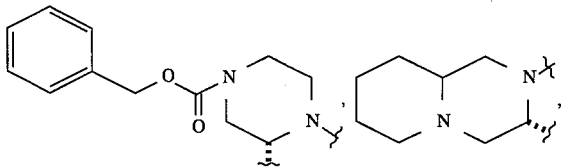

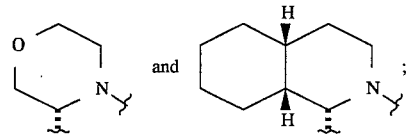

$R^3$ is selected from the group consisting of phenyl,

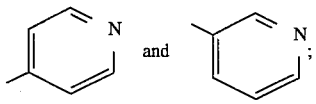

and $R^4$ is tert-butyl.

7. The process of claim 6 wherein $R^3$ is phenyl, and $R^1$ and $R^2$ together are

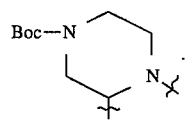

* * * * *